(12) United States Patent
Tanaka

(10) Patent No.: US 8,080,017 B2
(45) Date of Patent: Dec. 20, 2011

(54) INTRAOCULAR LENS INSERTION TOOL

(75) Inventor: Masayoshi Tanaka, Nagoya (JP)

(73) Assignee: Menicon Co., Ltd., Nagoya (JP)

( * ) Notice: Subject to any disclaimer, the term of this patent is extended or adjusted under 35 U.S.C. 154(b) by 206 days.

(21) Appl. No.: 12/318,227

(22) Filed: Dec. 23, 2008

(65) Prior Publication Data

US 2009/0171366 A1 Jul. 2, 2009

(30) Foreign Application Priority Data

Dec. 28, 2007 (JP) ................... 2007-341157

(51) Int. Cl.
*A61F 9/007* (2006.01)
(52) U.S. Cl. ....................... 606/107; 623/6.12
(58) Field of Classification Search .................. 606/107; 623/6.11, 6.12
See application file for complete search history.

(56) References Cited

U.S. PATENT DOCUMENTS

| | | | |
|---|---|---|---|
| 4,765,329 A * | 8/1988 | Cumming et al. | 606/107 |
| 5,728,102 A * | 3/1998 | Feingold et al. | 606/107 |
| 5,860,984 A * | 1/1999 | Chambers et al. | 606/107 |
| 5,876,406 A * | 3/1999 | Wolf et al. | 606/107 |
| 6,059,791 A * | 5/2000 | Chambers | 606/107 |
| 6,162,229 A * | 12/2000 | Feingold et al. | 606/107 |
| 6,723,104 B2 * | 4/2004 | Ott | 606/107 |
| 2002/0156486 A1 * | 10/2002 | Nadel | 606/107 |
| 2005/0149057 A1 | 7/2005 | Rathert | |
| 2006/0142780 A1 | 6/2006 | Pynson et al. | |

FOREIGN PATENT DOCUMENTS

| | | |
|---|---|---|
| EP | 1 424 048 A1 | 6/2004 |
| EP | 1 857 074 A1 | 11/2007 |
| JP | B2-07-079826 | 8/1995 |
| JP | B2-3412103 | 3/2003 |
| JP | B2-3420724 | 4/2003 |
| WO | WO 2004/091447 A2 | 10/2004 |

\* cited by examiner

*Primary Examiner* — Ryan Severson
(74) *Attorney, Agent, or Firm* — Oliff & Berridge, PLC

(57) ABSTRACT

An intraocular lens insertion tool with a tool body for accommodating an intraocular lens and adapted to insert into an eye the intraocular lens through displacement of the lens in an axial forward direction by a plunging member, and to push out the lens through an insertion tube section disposed at an axial distal end of the tool body. The insertion tube section has an inclined orifice that opens on diagonal to the center axis of the insertion tube section. The plunger member has a sliding part that during displacement thereof in a direction of plunging into the tool body will slide against the tool body. A resistance graduating mechanism is provided for gradually increasing operation resistance of the plunger member by gradually increasing contact force on the sliding part as the lens gradually emerges from the inclined orifice through plunging of the plunger member into the tool body.

8 Claims, 14 Drawing Sheets

INTRAOCULAR LENS INSERTION TOOL

INCORPORATED BY REFERENCE

The disclosure of Japanese Patent Application No. 2007-341157 filed on Dec. 28, 2007 including the specification, drawings and abstract is incorporated herein by reference in its entirety.

BACKGROUND OF THE INVENTION

1. Field of the Invention

The present invention relates to an intraocular lens insertion tool used to insert an intraocular lens into the eye.

2. Description of the Related Art

One method employed in the past in the field of cataract surgery involves extracting the intracapsular crystalline lens through a surgical incision made in ocular tissue such as the cornea (sclera) or anterior capsule section of the crystalline lens, and once the crystalline lens has been removed, inserting an intraocular lens serving as a replacement for the crystalline lens back through the incision and positioning it within the capsule.

Particularly in recent years, methods that employ an intraocular lens insertion tool like that disclosed in Japanese Patent No. 3412103 or Japanese Patent No. 3420724 have come into widespread use. Typically, the intraocular lens will be inserted into the eye by first inserting the distal orifice of an insertion tube provided at the distal end section of the body of the tool through a surgical incision, then pushing the intraocular lens (which has been maintained in a state of compact deformation inside the body of the tool) out through the distal orifice of the insertion tube. By employing such an insertion tool, the intraocular lens can be inserted into the eye without expanding the surgical incision that was made for the purpose of extracting the crystalline lens, thereby reducing the labor entailed in the surgical operation, as well as reducing the risk of post-surgical astigmatism or infection.

One requirement of an intraocular lens insertion tool of this type is excellent ease of control so that the surgeon will be able to consistently perform delicate operations with high precision during a surgical operation. This ease of control refers to the ability of the surgeon to carry out the lens ocular insertion procedure in the intended fashion, and requires that the intraocular lens be pushed and inserted into the eye at the intended location, in the intended condition and at the intended speed.

To meet this need, there has been proposed, for example in Japanese examined Patent Publication No. JP-B-07-079826, an insertion tool furnished in the interior of the insertion tool with a first stage drive mechanism adapted to push and advance the intraocular lens at high speed to a location slightly prior to that at which the lens is pushed out from the insertion tool, and a second stage drive mechanism adapted to subsequently push and advance the intraocular lens at low speed. According to this insertion tool, the overall procedure time of the plunging step can be reduced by advancing the intraocular lens at high speed by the first stage drive mechanism, while at the same time ensuring careful insertion into the eye by advancing the intraocular lens at low speed by the second stage drive mechanism when the intraocular lens is pushed out from the insertion tool.

However, an insertion tool like that disclosed in JP-B-07-079826 is merely a design adapted to increase the plunging speed of the plunger member in the approach zone, as such, it affords no particular advantages in relation to the lens insertion procedure per se. This insertion tool is not capable of permitting the surgeon to carry out the lens ocular insertion procedure in the intended fashion. Specifically, it is necessary for the surgeon to insert the lens into the eye at his or her own chosen speed, making it undesirable for a sudden change in perceived speed of pushing of the lens to occur at a moment just prior to pushing out the lens. That is, in order enable the surgeon to carry out the lens ocular insertion procedure in the intended fashion, it will be desirable for the surgeon, working with a constant level of pressing force, to be able to move the plunger member at constant speed up to the end and to insert the intraocular lens into the eye at constant speed.

If insertion tools of conventional design are examined from this standpoint, a satisfactory insertion tool has yet to be encountered.

As mentioned previously, the intraocular lens is made of elastic material so as to allow the surgical incision to be smaller during insertion, and will be inserted into the eye while held in a compacted (e.g. a folded or rolled) state within the insertion tube section of the insertion tool. For this reason, when the intraocular lens is pushed out from the distal end orifice of the insertion tube section within the eye, the intraocular lens will exhibit recovery so as to expand based on its inherent elasticity in the course of being pushed out partially from the distal end orifice. As result of this recovery force acting on the distal end orifice, the reaction force produced thereby will act in a direction causing the lens to be ejected from the insertion tube section.

For this reason, despite the fact that the surgeon operates the plunger member with a constant level of force, as result of the ejecting action produced by the elasticity of the intraocular lens per se, resistance against pushing of the plunger member will decrease gradually, owing to additive action of elastic recovery force and a reduction in sliding resistance of the intraocular lens with respect to the insertion tube. As a result, the intraocular lens may become pushed out at high speed before the surgeon realizes it, with a risk that the lens will ultimately pop out into the eye. This will make it difficult for the surgeon to accomplish insertion in the intended fashion, and poses a significant problem in terms of the surgeon being able to accomplish the insertion procedure in the intended fashion.

Even where the insertion tool, like that disclosed in JP-B-07-079826, has been designed to shift the plunging speed to low speed at a stage prior to traveling the prescribed distance, insofar as a plunging operation at constant force at a prescribed stroke is employed, the problem of a tendency for the intraocular lens to experience decreasing resistance at an accelerating rate as it is pushed out from the distal end orifice so that the intraocular lens flies out before the surgeon realizes it, will remain unchanged.

To address this problem, as with the insertion tool disclosed in U.S. Pat. No. 4,765,329 for example, the idea has been entertained to incorporate a coil spring and to gradually vary the operating force of the plunger member. However, with the insertion tool disclosed in U.S. Pat. No. 4,765,329, there will be an unavoidable increase in the number of parts and the number of assembly steps; and more than anything else the need for space for installation of the coil spring will make the insertion tool larger in scale and increase its weight, resulting in problems such as diminished control. Practical utility will be poor as a result.

SUMMARY OF THE INVENTION

It is therefore one object of this invention to provide an intraocular lens insertion tool of novel design having a simple design and adapted to push the intraocular lens at generally unchanging speed through the entire plunging step.

The modes of the present invention addressed to solving the aforementioned objects will be discussed below. The constituent elements employed in each mode may be employed in any possible combination.

A first mode of the present invention provides a tool body having generally tubular shape for accommodating an intraocular lens, and including an insertion tube section disposed at an distal end section of the tool body in an axial direction; and a plunging member inserted into the tool body from a rear in the axial direction and moved forward for inserting into an eye the intraocular lens such that the intraocular lens undergoes compact deformation in association with forward displacement in the axial direction by the plunging member and is pushed out through the insertion tube section, wherein the insertion tube section has at a distal end thereof an inclined orifice that opens on diagonal with respect to an center axis of the insertion tube section, the plunger member is furnished with a sliding part that slides against the tool body during displacement thereof in a direction of plunging into the tool body, and a resistance graduating mechanism is provided for gradually increasing operation resistance of the plunger member by gradually increasing contact force exerted on the sliding part as the intraocular lens gradually emerges from the inclined orifice through plunging of the plunger member into the tool body.

In the intraocular lens insertion tool constructed according to the present mode, the intraocular lens can be pushed at generally unchanging speed throughout the entire intraocular lens plunging process. Specifically, according to the present mode, because the distal end orifice of the insertion tube section is defined as an inclined orifice which is inclined, the intraocular lens will gradually emerge through the inclined orifice in association with increasing plunging distance of the plunger member. It will therefore be possible to prevent the intraocular lens from experiencing a sudden release of ejecting action due to its elasticity, causing the intraocular lens to pop out from the distal end orifice, such as can occur with a distal end orifice of simple circular shape produced by cutting perpendicular to the center axis of the insertion tube section.

Here, as the intraocular lens gradually emerges through the inclined orifice, the ejecting action will gradually increase owing to additive action of inherent elastic recovery force of the lens and a reduction in sliding resistance with respect to the insertion tube section. However, in the insertion tool constructed in accordance with the present mode, due to the provision of a resistance graduating mechanism adapted to gradually increase the contact force exerted on a sliding part that has been provided to the plunger member, the operating resistance of the plunger member will gradually increase as the intraocular lens emerges so that the ejecting action exerted by the plunger member can be gradually reduced. It will be possible thereby to avoid a situation in which accelerating ejection action is exerted on the intraocular lens before the surgeon realizes it, and to push the intraocular lens along at generally constant speed through the entire plunging process. In other words, using the resistance graduating mechanism, it will be possible to compensate for the gradual reduction of operating resistance of the plunger member in association with the intraocular lens emerging through the inclined orifice. Through use of the inclined orifice and the resistance graduating mechanism in combination, it will be to present the surgeon with a generally constant level of operating resistance throughout the entire plunging process. The surgeon will then be able to move the plunger member at constant speed to completion through the action of constant plunging force, making it possible as a result to insert the intraocular lens at constant speed.

Furthermore, in the insertion tool constructed in accordance with the present mode, it is possible to achieve the resistance graduating mechanism through a simple design, namely, that of gradually increasing contact force on the sliding part provided to the plunger member. As there will be no need to incorporate special components such as a coil spring of the insertion tool disclosed in U.S. Pat. No. 4,765,329 discussed earlier for example, the insertion tool can have a more compact and lightweight design, improving its ease of handling and control.

A second mode of the present invention provides an intraocular lens insertion tool according to the first mode, wherein the resistance graduating mechanism is constituted by providing an inclined face inclined with respect to a plunging direction of the plunger member, to at least one of the sliding part of the plunger member, and a contact portion provided on the tool body and adapted to slide against the sliding part during plunging of the plunger member.

In the intraocular lens insertion tool constructed according to the present mode, as the height of the inclined face gradually increases the level of deformation of the contact portion and/or sliding part positioned in contact against the inclined face will increase gradually as well. An increase in elastic force produced by this deformation, and hence an increase in the magnitude of the contact load exerted as reaction force on the sliding part via the inclined face will result. Here, since the operating resistance of the plunger member is contact resistance, frictional force will not change; only normal force will change. As a result, the operating resistance of the plunger member will gradually increase. By so doing, the resistance graduating mechanism can be implemented with a simple design, with no need for any additional parts.

At the same time, by utilizing elastic deformation of the sliding part and/or the contact portion, elastic force can be made gradually larger in association with increasing plunging distance of the plunger member, so that the contact load exerted across the tool body and the plunger member can be increased smoothly, and operating resistance can be varied smoothly. Moreover, through adjustment of the shape of inclined face and of the sliding part and/or the contact portion disposed in contact against the inclined face, operating resistance of the plunger member can be adjusted precisely.

A third mode of the present invention provides an intraocular lens insertion tool according to the first or second mode, wherein the resistance graduating mechanism is constituted by providing in the tool body a contact portion adapted to slide against the sliding part during plunging of the plunger member; forming a deflection zone adapted to produce elastic deformation of the plunger member in a prescribed lengthwise section of the axial direction through pressing of the contact portion against the sliding part; and forming in the deflection zone a cross section variation portion of gradually increasing cross sectional area of the plunger member in the plunging direction of the plunger member.

In the intraocular lens insertion tool constructed according to the present mode, in association with increasing cross sectional area of the plunger member in the deflection zone, perpendicular reaction force on the deflection zone (which acts as reaction force of deflection of the plunger member) will gradually change, and hence frictional resistance of the contact portion will gradually increase. As a result, contact force exerted on the sliding part will gradually become larger, and operating resistance of the plunger member will gradually increase. By so doing, the deflection reaction force of the plunger member itself can be utilized advantageously to achieve a resistance graduating mechanism of simple design. At the same time, the advantageous utilization of deflection of the plunger member, frictional resistance can be increased smoothly in association with increasing plunging distance of the plunger member, and operating resistance can be varied smoothly.

A fourth mode of the present invention provides an intraocular lens insertion tool according to any of the first to third modes, wherein the insertion tube section is formed by a light-transmissive component; and a visible marker line extending in a circumferential direction of the insertion tube section is formed at a prescribed location axially to a rear of the inclined orifice in the insertion tube section.

In the intraocular lens insertion tool constructed according to the present mode, the marker line can be used as an air bleed hole during pushing of the intraocular lens. With this arrangement, pushing of the intraocular lens can be carried out more smoothly. Furthermore, since the insertion tube section is made of a light-transmissive component and the marker line is visible from the outside, by forming the marker line at an appropriate location it will be possible to use the line as a mark during the insertion procedure. For example, by way of the prescribed location at which to form the marker line, by forming the marker line at a location that, with the insertion tube section inserted into the surgical incision, will be aligned with the surgical incision, it can be used as a mark to indicate the location of insertion into the surgical incision. The marker line in the present mode may be used concomitantly as an indicator mark for both an air bleed hole and the insertion location, or for one or the other of these. It would also be possible to form a plurality of marker lines.

A fifth mode of the present invention provides an intraocular lens insertion tool according to any of the first to fourth modes wherein the intraocular lens is provided with a pair of haptics that extend to either side; and these haptics are set facing in axial direction of the tool body, with the haptic situated to the rear in the axial direction being adapted to be positioned in a notch that is disposed at the distal end section of the plunger member.

In the intraocular lens insertion tool constructed according to the present mode, by positioning a haptic situated on the plunger member side in a notch made in the plunger member, it will be possible for the haptic to escape from between the plunger member and the body of the intraocular lens, making it possible for the body of the intraocular lens and the plunger member to face one another directly. Since the plunger member can thus be disposed in direct contact with the body of the intraocular lens when plunging is initiated, it will be possible to avoid entanglement of the haptic, so that plunging can be carried out more consistently.

A sixth mode of the present invention provides an intraocular lens insertion tool according to any of the first to fifth modes, wherein the tool body is furnished with a resting portion disposed in communication with the basal end of the insertion tube section; a resting face on which the intraocular lens rests and an opening that opens to the outside of the tool body are formed in the resting portion; and the tool body is furnished with a cover body disposed covering the opening, with the plunger member pushed towards the resting face by the cover body.

In the intraocular lens insertion tool constructed according to the present mode, by pushing the plunger member with the cover body, unwanted deformation (particularly unwanted uplift from the resting face) of the plunger member can be effectively inhibited, and a more stable plunging operation can be carried out.

A seventh mode of the present invention provides an intraocular lens insertion tool according to the sixth mode, wherein a pair of guide projecting parts extending in the axial direction are formed on the bottom face at an axial front of the resting face in the tool body, and the plunger member is guided between these guide projecting parts.

In the intraocular lens insertion tool constructed according to the present mode, because the plunger member can be guided in the axial direction of the tool body while positioned between the guide projecting parts, unwanted deformation (particularly unwanted displacement in the axis-perpendicular direction of the resting face) of the plunger member can be effectively inhibited, and a more stable plunging operation can be carried out.

An eighth mode of the present invention provides an intraocular lens insertion tool according to any of the first to seventh modes, wherein a step adapted to contact the plunger member inside a plunging zone of the plunger member is provided in the tool body.

In the intraocular lens insertion tool constructed according to the present mode, due to the plunger member coming into contact against the step, a restraining sensation can be imparted to the surgeon during the plunging operation. This restraining sensation will enable the surgeon to ascertain the current location of the intraocular lens, and will prompt attention to the operation at hand, calling attention to the fact that inter alia that careful operation will be necessary from the point in time that the restraining sensation is perceived. A plurality of steps may be formed in the plunging zone of the plunger member.

A ninth mode of the present invention provides an intraocular lens insertion tool according to any of the first to eighth modes, wherein through-holes are formed in the resting face on which the intraocular lens rests, a support member defined as a separate part from the tool body is attached to the resting face from the outside, and an outside peripheral support portion for supporting the outside peripheral portion of the intraocular lens is constituted by passing support portions formed on the support member through the through-holes so as to project out above the resting face; and catch hooks adapted to catch on the resting face and prevent the support portions from dislodging from the resting face and to maintain the support portions in a state projecting out from the resting face are formed on the support portions.

In the intraocular lens insertion tool constructed according to the present mode, by providing support to the outside peripheral section of the intraocular lens, the intraocular lens can be supported in a noncontact state with respect to its center section, which can affect the optical characteristics. The risk of possible damage to the center section of the intraocular lens can be reduced thereby. Moreover, when the intraocular lens is disposed resting on the resting face, the intraocular lens can be positioned resting on the resting face by a simple operation, namely, of removing the support member so that the outside peripheral support portions projecting up from the resting face retract below the resting face, allowing the surgeon to easily set up the intraocular lens.

Furthermore, in the present mode, by means of the catch hooks it is possible to consistently maintain a state in which the support portions project out from the resting face, in other words, a state in which the support member is attached to the tool body. In the present mode in particular, because catch hooks have been formed on the support portions, the support portions can directly engage the resting face, making it possible to reduce chattering by the support portion, and improving the positional stability of intraocular lens in the retained state. Further, by forming catch hooks on the support portions, a locking mechanism for attaching the support member to the tool body can be achieved with exceptional space efficiency and production efficiency.

BRIEF DESCRIPTION OF THE DRAWINGS

The foregoing and/or other objects features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
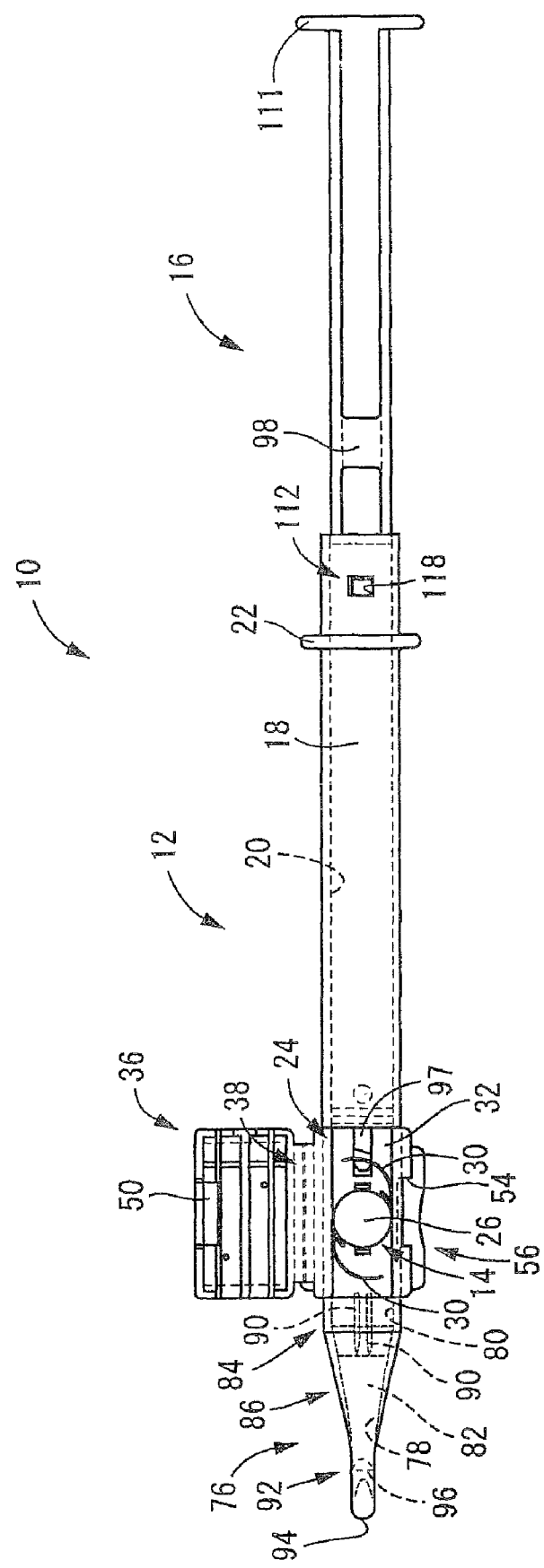
FIG. 1 is a top plane view of an intraocular lens insertion tool according to a first embodiment of the present invention.
Figure 2:
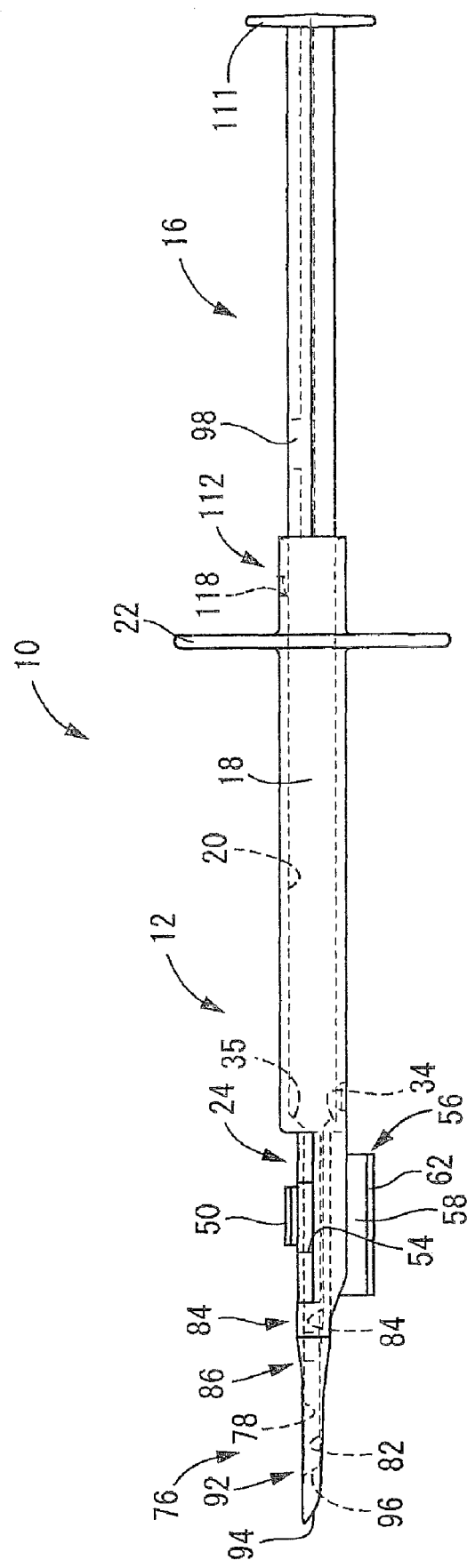
FIG. 2 is a side elevational view of the intraocular lens insertion tool of FIG. 1.
Figure 3:
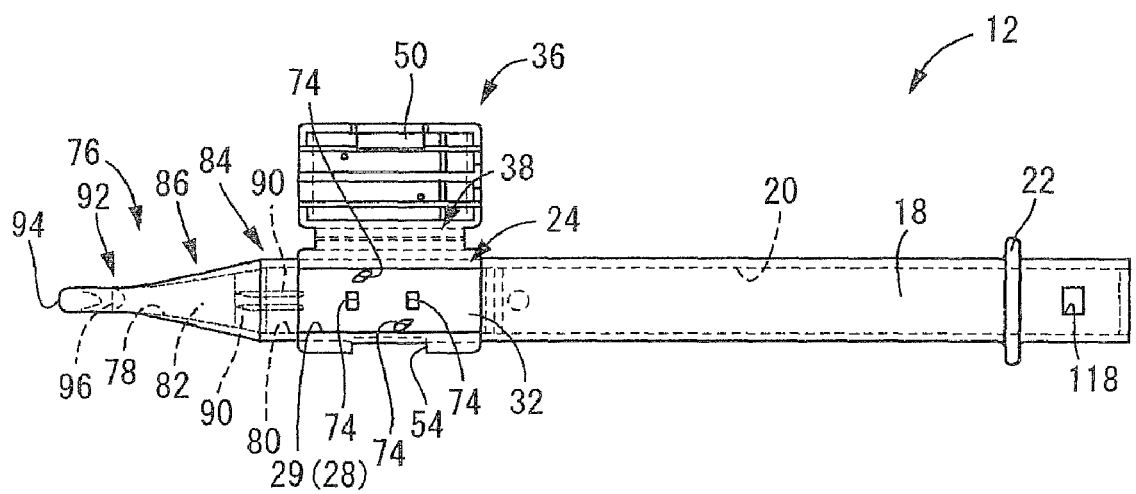
FIG. 3 is a top plane view of a tool body of the intraocular lens insertion tool of FIG. 1.
Figure 4:
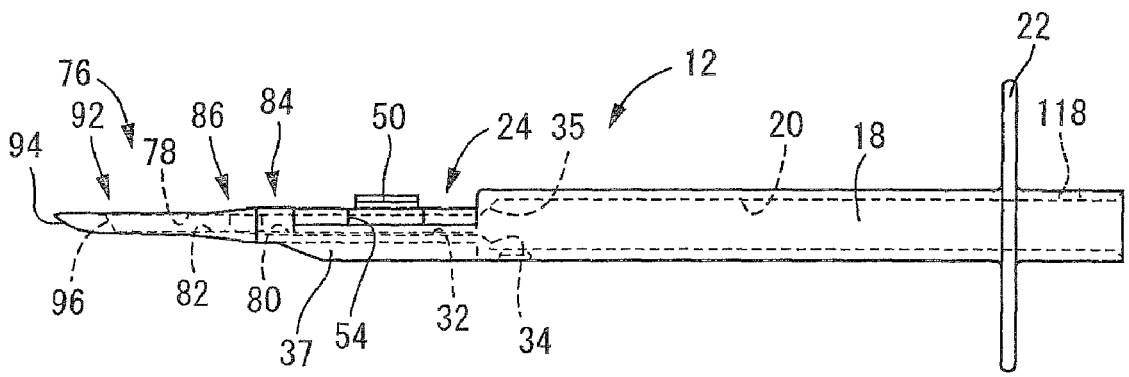
FIG. 4 is a side elevational view of the tool body of FIG. 3.
Figure 5:
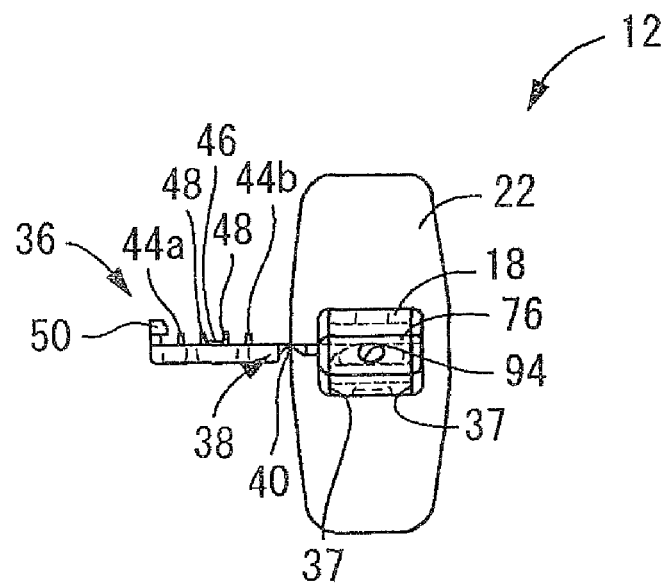
FIG. 5 is a front elevational view of the tool body of FIG. 3.
Figure 6:
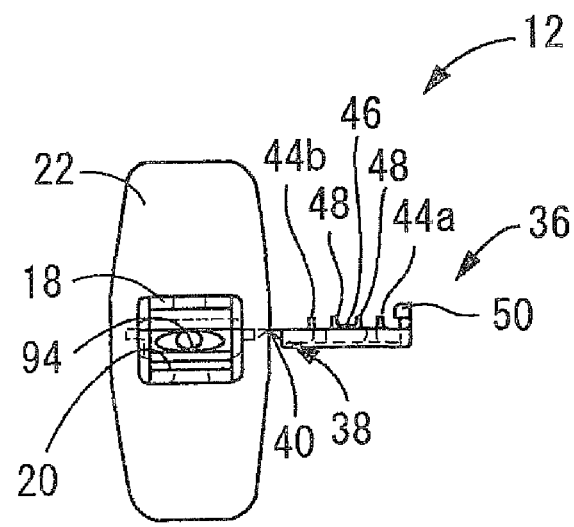
FIG. 6 is a rear elevational view of the tool body of FIG. 3.

First, an intraocular lens insertion tool 10 according to a first embodiment of the present invention is depicted in FIGS. 1 and 2. The insertion tool 10 is adapted to accommodate an intraocular lens 14 in the interior of a tool body 12 having generally tubular shape perforated in its interior throughout its entire length and open at the front and back ends, into which inserts a plunger 16 serving as a plunger member. Herein, 'front' refers to the plunging direction of the plunger 16 (leftward in FIG. 1), and 'upward' refers to the upward direction in FIG. 2. 'Left-right direction' refers to the left-right direction of the insertion tool 10 in rear view (in FIG. 1, the upward direction is right and the downward direction is left).

To describe in greater detail, as depicted in FIGS. 3 to 6, the tool body 12 has a main tubular section 18 of generally tubular shape. A through-bore 20 is formed in the interior of the main tubular section 18 and with generally oblong cross section passes therethrough in the axial direction. A plate-like portion 22 that extends on the perpendicular to the direction of extension of the main tubular section 18 is integrally formed at a location somewhat to the front of the back end of the main tubular section 18.

Figure 7:
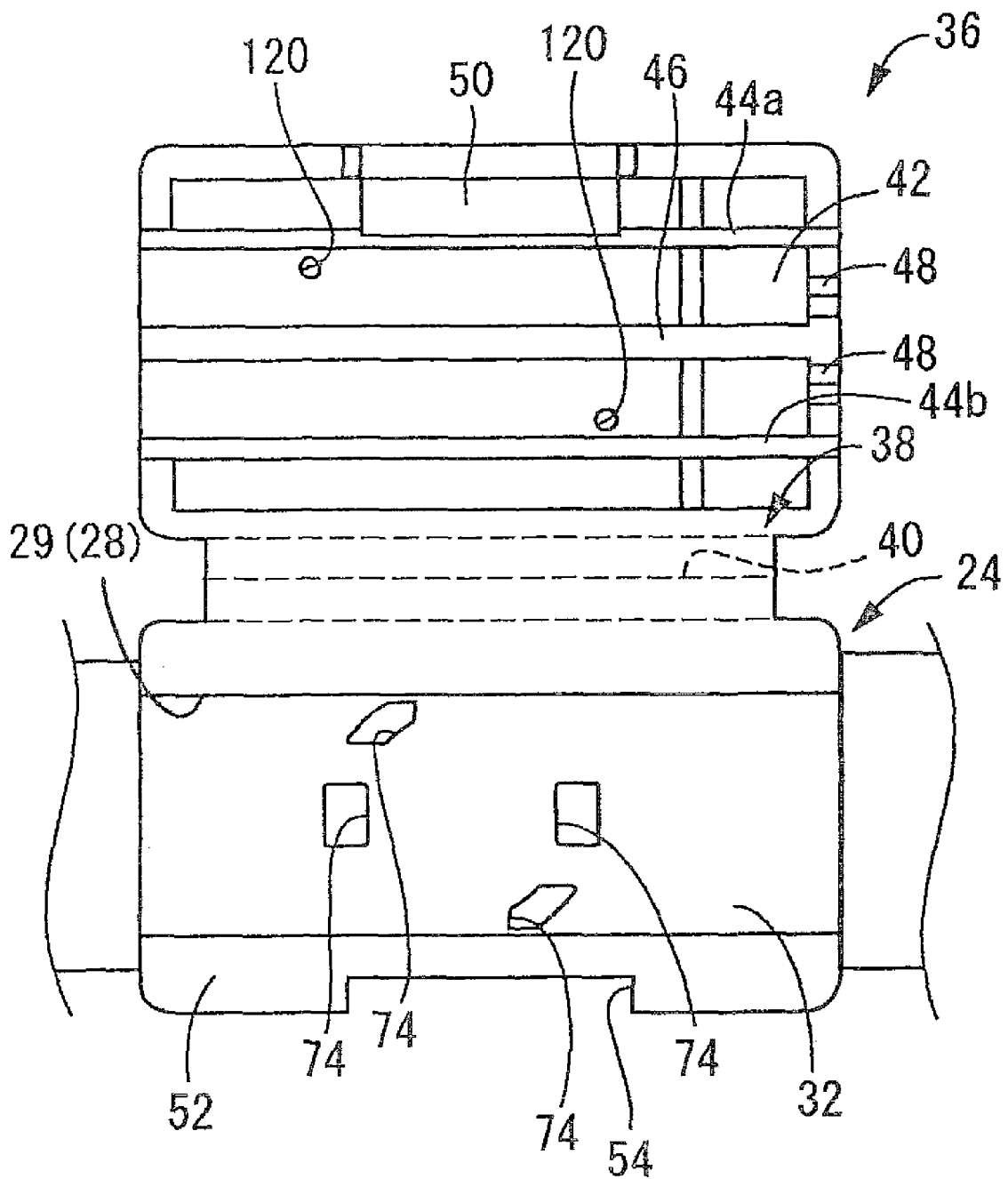
FIG. 7 is a fragmentary enlarged top plane view of the tool body of FIG. 3.

A stage 24 is provided as a resting portion at the front of the main tubular section 18 in the tool body 12. FIG. 7 depicts the stage 24. In the stage 24 there is formed a recessed slot 28 of width dimension slightly larger than the diameter dimension of the main body 26 of the intraocular lens 14 and extending in the axial direction. The recessed slot 28 has lengthwise dimension in the axial direction that is somewhat larger than the maximum width dimension (dimension in the left-right direction in FIG. 1) of the intraocular lens 14 inclusive of haptics 30, 30 that extend to either side thereof.

Here, the recessed slot 28 has an opening 29 that opens upward, and a resting face 32 that is formed on its base face. The resting face 32 is defined by a flat face having width dimension slightly larger than the minimum width dimension (dimension in the vertical direction in FIG. 1) of the intraocular lens 14, and lengthwise dimension in the axial direction that is larger than the maximum width dimension (dimension in the left-right direction in FIG. 1) of the intraocular lens 14. The heightwise position of the resting face 32 is such that it is situated above the heightwise position of the base face of the through-bore 20 in the main tubular section 18; a lower wall part 34 (see FIG. 4) is formed at the front edge part of the through-bore 20 in the main tubular section 18 and extends upward from the base face of the through-bore 20 to connect with the back edge part of the resting face 32. By so doing the recessed slot 28 will communicate with the through-bore 20, and the width dimension of the recessed slot 28 will be approximately equal to the width dimension of the through-bore 20. An upper wall part 35, provided as a contact portion that extends forward and downward on the diagonal from the upper face of the through-bore 20, is formed above the front edge of the through-bore 20. Downward projecting walls 37, 37 are formed projecting downward from the widthwise side edges of the resting face 32.

To the side of the recessed slot 28 (in the present embodiment, the right side), a cover part 36 provided as the cover body is integrally formed with the tool body 12. The cover part 36 is formed with an axial direction dimension approximately equal to the axial direction dimension of the recessed slot 28, and with a width dimension somewhat larger than the width dimension of the recessed slot 28. The cover part 36 is linked to the tool body 12 by a linking part 38 of generally thin plate shape formed by extending the upper edge of the stage 24 to the side (in the present embodiment, the right side). The linking part 38 is thinnest in a bending part 40 that extends through its approximately widthwise center section in the axial direction of the tool body 12, and is adapted to bend in this bending part 40. The cover part 36 can thereby be superposed over the recessed slot 28 by bending the linking part 38, so as to cover the opening 29.

On an opposed face 42 (the face positioned in opposition to the resting face 32) of the cover part 36 there are integrally formed a pair of left and right guide plate parts 44a, 44b provided by way of a pair of guide projections extending in the axial direction of the tool body 12. These left and right guide plate parts 44a, 44b are formed along the entire axial extension of the cover part 36, with the distance between their opposing faces being somewhat smaller than the width dimension of the recessed slot 28. The outside peripheral edge of the opposed face 42 is slightly thicker about the entire periphery, and the left and right guide plate parts 44a, 44b project out beyond the outside peripheral edge of the opposed face 42.

A center guide plate part 46 provided as a guide projection that extends parallel with the left and right guide plate parts 44a, 44b in the axial direction of the tool body 12 is integrally formed on the opposed face 42, at the approximate center location between the opposing faces of the left and right guide plate parts 44a, 44b. The center guide plate part 46 has a heightwise dimension such that it projects slightly out from the thick outside peripheral edge of the opposed face 42, and is integrally formed so as to extend from the outside peripheral edge along the entire length of the opposed face 42 in the axial direction. A pair of guide projections 48, 48 are formed to either side of the center guide plate part 46 in the zone of connection of the outside peripheral edge of the opposed face 42 with the axial rear edge of the center guide plate part 46. The guide projections 48 have generally triangular cross section and are integrally formed so as to project up from the outside peripheral edge of the opposed face 42, the projecting dimension thereof being approximately equal to the projecting dimension of the left and right guide plate parts 44a, 44b.

Additionally, a catch piece 50 is formed on the cover part 36 on the edge lying opposite from the linking part 38. An outwardly projecting projecting edge part 52 is formed on the stage 24 on the edge thereof lying opposite from the cover part 36; and a catch notch 54 is formed in the projecting edge part 52 at a location corresponding to this catch piece 50.

Figure 8:
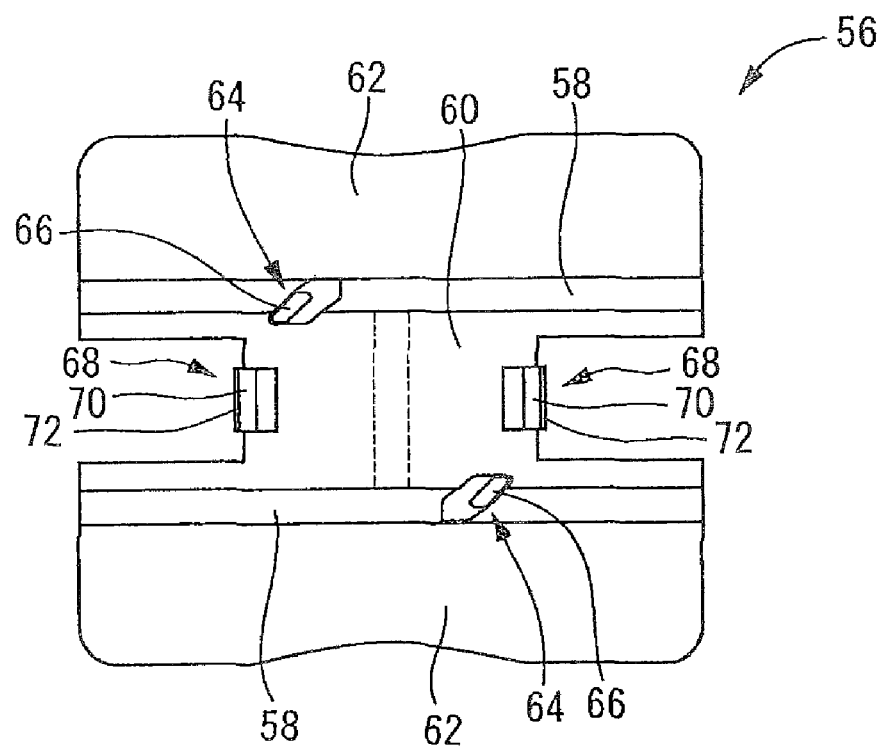
FIG. 8 is an top plane view of a support member of the intraocular lens insertion tool of FIG. 1.
Figure 9:
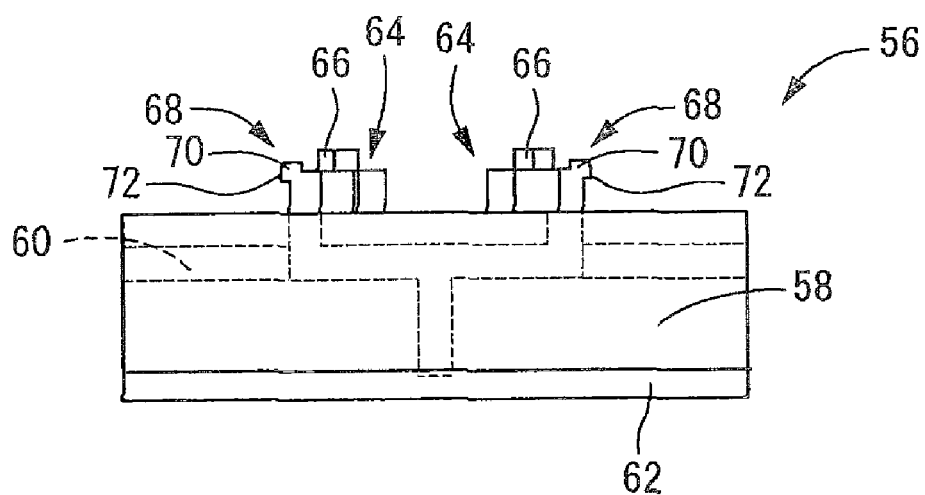
FIG. 9 is a side elevational view of the support member of FIG. 8.

A support member 56 is detachably disposed below the resting face 32 of the stage 24 having the above construction. As depicted in FIGS. 8 and 9, the support member 56 is constituted as a separate member from the tool body 12, and is constructed of a pair of side wall parts 58, 58 linked by a linking plate part 60 between their opposing faces. Here, the distance separating the outside faces of the side wall parts 58 will be approximately equal to the diameter dimension of the main body 26 of the intraocular lens 14. A leg plate part 62 that projects out and flares outwardly is integrally formed on the lower edge of each of the side wall parts 58. The leg plate part 62 has a slightly recessed contour in the center section in the axial direction in top view.

At the upper edge part of each of the side wall parts 58, 58 there is integrally formed a first support part 64 provided as a support portion that projects upward in generally arcuate contour in top view. In the outside section of the upper end face of each first support part 64, a projecting peripheral wall 66 is integrally formed towards the inward side of the support member 56. Here, the distance separating the peripheral walls 66 will be slightly larger than the diameter dimension of the main body 26 of the intraocular lens 14.

A pair of second support parts 68, 68 provided as support portions that project upwardly with oblong shape in top view are integrally formed at both axial ends of the linking plate part 60. Here, the heightwise location of the upper end faces of the second support parts 68 are equivalent to the heightwise location of the upper end faces of the first support parts 64. Additionally, on the upper face of each second support part 68, towards the outside of the support member 56, there is integrally formed a peripheral wall 70 that projects upward along the entire width of the second support part 68; the distance separating the peripheral walls 70 will be slightly larger than the diameter dimension of the main body 26 of the intraocular lens 14. Also, a catch hook 72 that projects slightly outward is formed along the entire width of the second support part 68 at its upper edge.

The support member 56 having the above construction is adapted for attachment from below the resting face 32 of the tool body 12. Specifically, through-holes 74 formed in the resting face 32 of the tool body 12 pass through it in the thickness direction. The through-holes 74 have shape similar to but slightly larger than that of the first support parts 64 and the second support parts 68 in top view. The first support parts 64 and the second support parts 68 of the support member 56 will be passed through the through-holes 74 from the lower side of the resting face 32 so as to project above the resting face 32. By so doing, the catch hooks 72 provided to the second support parts 68 will project above the resting face 32 and become engaged with the upper face of the resting face 32, thereby preventing the first support parts 64 and the second support parts 68 from becoming detached, and holding the support member 56 in a state of attachment from the outside of the tool body 12 with the first support parts 64 and the second support parts 68 projecting above the resting face 32. In the present embodiment, the catch hooks 72 are included in the locking mechanism that locks the support member 56 to the tool body 12.

Figure 10:
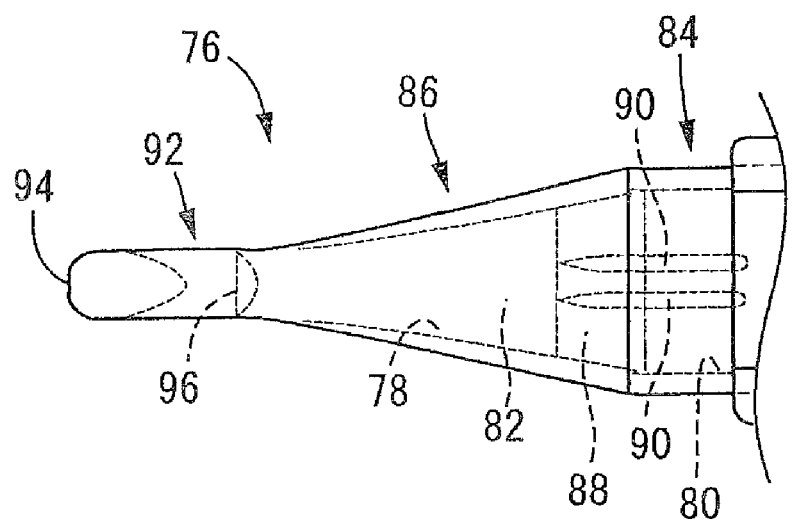
FIG. 10 is a top plane view of an insertion tube section of the intraocular lens insertion tool of FIG. 1.
Figure 11:
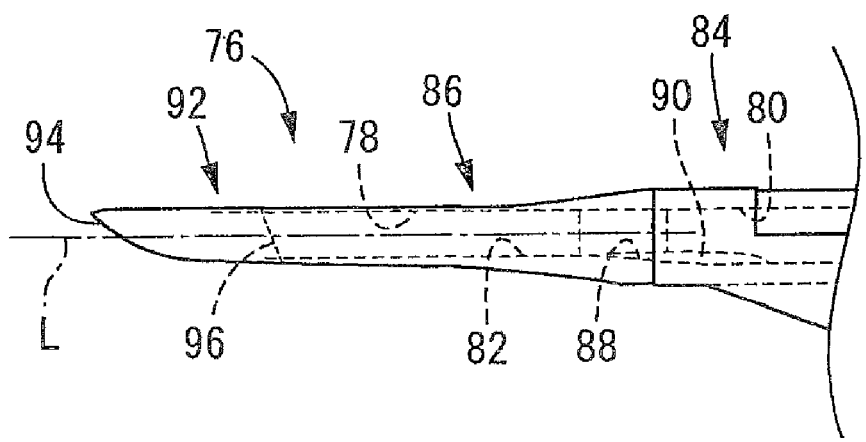
FIG. 11 is a side elevational view of the insertion tube section of FIG. 10.

Additionally, a nozzle part 76 provided as an insertion tube section is integrally formed at the axial distal end of the tool body 12, to the front of the stage 24. The nozzle part 76 is depicted in FIGS. 10 and 11. The nozzle part 76 as a whole has outside contours that gradually narrow from the basal end (towards the stage 24) towards the distal end in the direction of its extension, and has a bore 78 that passes through its entire length in the direction of its extension.

The bore 78 communicates with the stage 24 through connection of a basal end orifice 80 that opens towards the stage 24 to the resting face 32. The basal end orifice 80 as a whole has a flattened, generally elliptical cross section with a base face 82 defined by a flat face, and an upper face with a generally arcuate contour. Here, a guide part 84 formed by the base face 82 connecting steplessly to the resting face 32 is formed in the bore 78. The guide part 84 has a flattened, generally elliptical cross section, and extends in the axial direction of the tool body 12 with generally unchanging width dimension and height dimension from the basal end orifice 80.

Also formed in the bore 78 is a constricted-diameter part 86 that communicates with the guide part 84 to the front of the guide part 84, and that has gradually decreasing cross sectional area. The constricted-diameter part 86 decreases in cross sectional area towards its distal end owing to decreasing width dimension of the base face 82 and the upper face. On the base face 82 of the back end section of the constricted-diameter part 86 there is formed an inclined face 88 that inclines gradually upward towards the front in the axial direction, and this inclined face 88 provides a step on the base face 82 of the bore 78. The upper face of the bore 78 is defined over its entire length in the axial direction by a stepless flat face, and the heightwise position of the upper face of the bore 78 is generally unchanging along its entire length in the axial direction.

Additionally, a pair of guide projecting parts 90 that extend in the axial direction of the tool body 12 with the widthwise center section of the base face 82 between them is formed on the base face 82 of the guide part 84 and the constricted-diameter part 86. The guide projecting parts 90 have linear contours that project slightly up from the base face 82 and extend parallel to one another, with axial length dimension such that their front edge part in the axial direction will be positioned at a location equivalent to the frontside edge of the inclined face 88, and their back edges in the axial direction will project slightly rearward in the axial direction from the basal end orifice 80. Here, by making the axial front edge section of the guide projecting parts 90 formed on the inclined face 88 slightly higher towards the front of the inclined face 88 in the axial direction, at the front edge of the inclined face 88 in the axial direction, they will have a heightwise position equivalent to the inclined face 88.

Furthermore, in preferred practice the guide projecting parts 90 will be arranged approximately parallel a prescribed distance apart from one another in the axis-perpendicular direction of the tool body 12 with the widthwise center of the base face 82 between them. The distance separating the guide projecting parts 90 will be slightly larger than the width dimension of the distal end part of the plunger member. In the present embodiment in particular, they are slightly larger than the width dimension of a rod-like part 100 of the plunger 16, described later.

In the nozzle part 76 to the front of the constricted-diameter part 86 in the axial direction, there is formed a distal end part 92 that extends in a straight path with generally unchanging cross sectional area. An inclined orifice 94 is formed at the distal edge of this distal end part 92. A recessed line 96, provided as a marker line, is formed at a prescribed location on the inside peripheral face of the distal end part 92, axially rearward from the inclined orifice 94. The recessed line 96 is defined by a slot that extends continuously around the entire circumference of the inside peripheral face of the distal end part 92 and that opens towards the inside of the distal end part 92. The recessed line 96 has diagonal contours in side view such that its upper section is formed to the front of its lower section, and in top view its upper section and lower section respectively extend in the axis-perpendicular direction of the distal end part 92. In the present embodiment in particular, the recessed line 96 will be formed with its upper section at a location 6 mm to the rear in the axial direction from the inclined orifice 94. The tool body 12 in the present embodiment is made from a component that is light-transmissive, and the recessed line 96 that has been formed on the inside peripheral face of the distal end part 92 will be visible from the outside. The inclined orifice 94 that has been formed at the axial distal edge of the nozzle part 76 is defined by an inclined orifice whose upper face extends further forward than the lower face, and that in side view is inclined with respect to the center axis: L of the nozzle part 76. In particular, in the present embodiment, as mentioned earlier, the tool body 12 inclusive of the nozzle part 76 and the main tubular section 18 is an integrally formed part; in addition to employing synthetic resin material having high transmittance of visible light as the material for making it, the peripheral wall of the nozzle part 76 and the stage 24 of the main tubular section 18 will be fashioned with sufficient thinness such that at least the outside contours of the intraocular lens 14 accommodated in the interior of the tool body 12 will be visible visually from the outside of the tool body 12. Accordingly, for the peripheral wall of the nozzle part 76 and the stage 24 of the main tubular section 18 in particular, it will be preferable to employ a resin-forming mold in which the mold faces for forming these sections have been designed with high precision approaching a mirror finish, so as to improve visibility of the intraocular lens 14 from the outside.

The specific structure of the recessed line 96 is not limited provided that it is visible from the outside. For example, in place of the recessed line 96, a raised line composed of a rib projecting out slightly from the inside peripheral face of the distal end part 92 could be used; or in place of the recessed line 96, a step could be produced by reducing thickness to the distal end side of the location in question. The recessed line 96 or raised line, step, or the like could also be formed on the outside peripheral face of the distal end part 92. Where formed on the outside peripheral face of the distal end part 92, a line colored through printing or other means could be provided in place of a raised line. Additionally, there is no need for the recessed line 96 or for the raised line, step, printed line etc. to form a continuous ring about the entire circumference of the nozzle part 76, and they may be formed over only portions of the circumference. Of course, it is not necessary for the line to be inclined with respect to the center axis, as it is in the present embodiment.

According to the present embodiment, the distal end part 92 is made of resin material having visible light transmittance, and thus the intraocular lens 14 being pushed along inside the nozzle part 76 will be visible from the outside; as noted, since the recessed line 96 is inclined with respect to the center axis in side view, during this process the recessed line 96 will approximately conform to the visible outline of the distal end part of the intraocular lens 14, which assumes a curled state as it is pushed through the interior of the nozzle part 76. For this reason, in relation to the location of the intraocular lens 14 as being pushed through the interior of the nozzle part 76, it will be possible to more easily discern when the location has reached one coincident with the recessed line 96.

The tool body 12 in the present embodiment described above is constituted as a single member integrally formed by the main tubular section 18, the stage 24, the cover part 36, and the nozzle part 76. The support member 56, which is constituted as a separate member from the tool body 12, is attached from below to the resting face 32. As mentioned above, the tool body 12 is a light-transmissive member, and even with the opening 29 of the stage 24 covered by the cover part 36, the intraocular lens 14 accommodated within the tool body 12 will be visible through the cover part 36.

Figure 12:
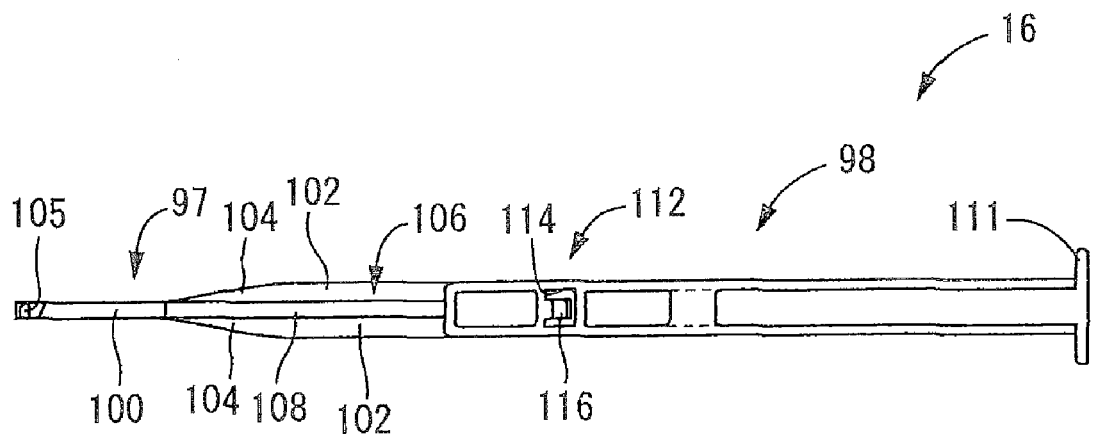
FIG. 12 is a top plane view of a plunger of the intraocular lens insertion tool of FIG. 1.
Figure 13:
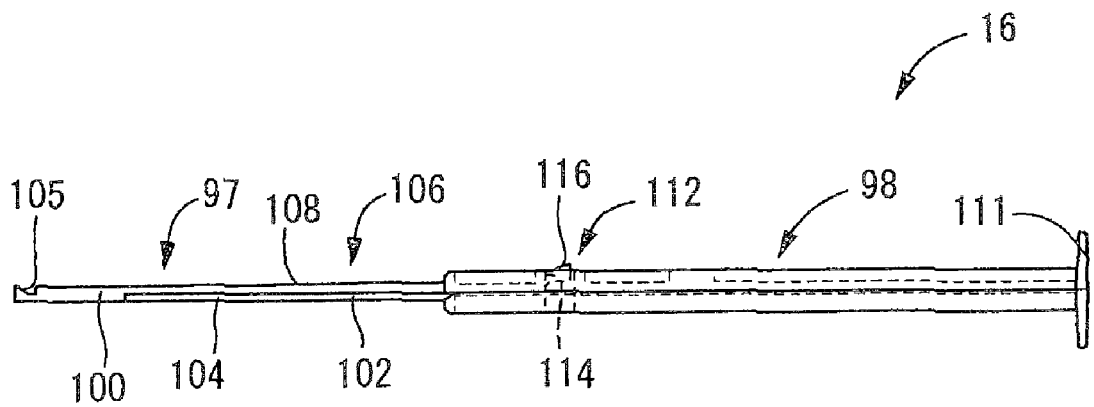
FIG. 13 is a side elevational view of the plunger of FIG. 12.

The plunger 16 which is provided as the plunger member is inserted into the through-bore 20 from the back of the tool body 12 having the above structure. The plunger 16 is depicted in FIGS. 12 and 13. The plunger 16 is of generally rod shape having axial length dimension somewhat larger than the axial length dimension of the tool body 12; and includes an integrally formed working part 97 of generally circular rod shape and a pass-through part 98 of generally oblong rod shape.

The working part 97 includes a rod-like part 100 of generally circular rod shape extending along the center axis of the plunger 16; and flattened parts 102 of thin plate form extending to either side in the width direction of the rod-like part 100. The flattened parts 102 extend from the back end of the rod-like part 100 towards the distal end direction with a width dimension equal to that of the pass-through part 98; and starting at the approximately medial section in the lengthwise direction of the rod-like part 100, have pointed parts 104 of gradually decreasing width dimension towards a zone somewhat rearward from the distal end part of the rod-like part 100. Here, the contours of the pointed parts 104 in top view conform to the horizontal cross section of the constricted-diameter part 86 in the nozzle part 76 of the tool body 12.

A notch 105 is formed in the axial distal end section of the working part 97. In the present embodiment, the notch 105 opens upward and to either side in the width direction; its inside peripheral face at the back end side in the axial direction in top view extends on the diagonal with respect to the axial direction of the working part 97 and spreads in the axis-perpendicular direction of the working part 97, while its inside peripheral face at the distal end side in the axial direction is defined as an inclined face that in top view extends in the axis-perpendicular direction of the working part 97 and inclines upward toward the distal end of the working part 97.

Additionally, an upward projecting portion 106 provided as an upwardly projecting sliding part is formed in the axial medial section of the working part 97. The upward projecting portion 106 has a width dimension equal to the width dimension of the rod-like part 100, and at a location somewhat to rear from the axial distal end section of the rod-like part 100 is provided with a tapered face 108 as an inclined face that inclines upward towards the rear and extends over a prescribed dimension in the axial direction. In the present embodiment in particular, the front edge part of the tapered face 108 is formed at the same location in the axial direction as are the front edges of the pointed parts 104, and the back edge section of the tapered face 108 is positioned at the axial back edge part of the rod-like part 100.

From the above it will be appreciated that the plunger 16 in the present embodiment has gradually increasing cross sectional area towards the rear in the axial direction, from the axial front edge parts to the axial back edge parts of the pointed parts 104 in the flattened parts 102, and from the axial front edge part to the axial back edge part of the tapered face 108.

Meanwhile, the pass-through part 98 has an axial dimension that is slightly larger than the axial dimension of the through-bore 20. The pass-through part 98 in substantially the entirety thereof has a generally "H" shaped transverse section whose width and height dimensions are slightly smaller than the width and height dimensions of the through-bore 20. A pusher plate 111 that spreads in the axis-perpendicular direction is integrally formed at the back edge part of the pass-through part 98.

Additionally, a catch part 112 provided as retaining means is formed somewhat to the front of the axial medial section of the pass-through part 98. On the catch part 112 there is formed a hook part 116 that juts into a through-hole 114 perforating the pass-through part 98 in the axis-perpendicular direction and projects upward from the pass-through part 98. With the plunger 16 passed through the main tubular section 18 of the tool body 12, the hook part 116 of the plunger 16 will come into engagement with a catch hole 118 perforating the upper face of the main tubular section 18 in the thickness direction, thereby holding the plunger 16 so that it is positioned relative to the tool body 12 while passing through it. The locations for forming the hook part 116 and the catch hole 118 are established such that, in the engaged state, the distal end part of the working part 97 will project out from the through-bore 20 of the tool body 12, and the notch 105 will be positioned so as to support from below the haptic 30 that is situated on the axial rearward side of the intraocular lens 14 accommodated in the stage 24, discussed later. The catch part 112 and the catch hole 118 may also be formed on the bottom face or side face of the insertion tool 10, for example.

In the intraocular lens insertion tool 10 having the above construction, first, the distal end section of the plunger 16 will be inserted from the rear into the main tubular section 18 of the tool body 12, and the hook part 116 will be urged into engagement with the catch hole 118 to position it at the initial position. Concomitantly therewith, the support member 56 will be attached to the tool body 12 from below the resting face 32 as described earlier. By so doing, the first support part 64 and the second support part 68 of the support member 56 will be held projecting up above the resting face 32.

Figure 14:
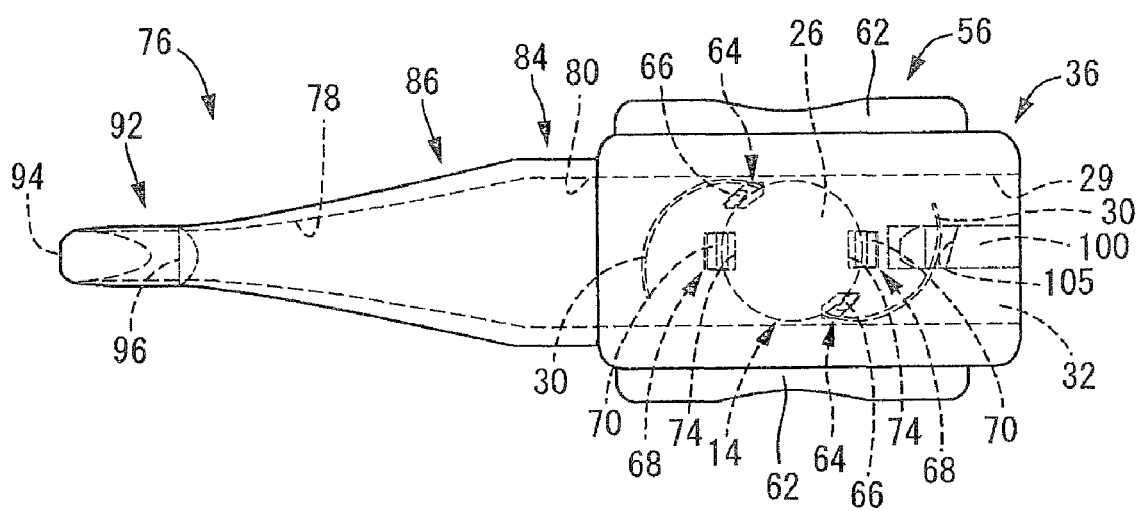
FIG. 14 is an enlarged top plane view of a principle part of the intraocular lens insertion tool of FIG. 1.

Then, as depicted in FIG. 14, the main body 26 of the intraocular lens 14 will be positioned resting on the upper end faces of the first support parts 64 and the second support parts 68, with the haptics 30, facing in the axial direction of the tool body 12. In FIG. 14, for ease in understanding, only the relevant section of the tool body 12, the intraocular lens 14, the first and second support parts 64, 68 that project above the resting face 32, and the distal end section of the plunger 16 facing into the stage 24, are shown. In this resting state, the intraocular lens 14 will be supported with the outside peripheral section of its main body 26 in a state of contact with the first and second support parts 64, 68, and with its center section in a noncontact state with the first and second support parts 64, 68. In the present embodiment, the first and second support parts 64, 68 are included in the constitution of an outside peripheral support part. In this resting state, the haptic 30 that in the intraocular lens 14 is the one situated toward the axial back side of the tool body 12 will be supported by the base face of the notch 105 of the plunger 16. Further, with the plunger 16 in the initial position, a second support part 68 that projects from the resting face 32 will be positioned to the axial front side of the plunger 16 (the left side in FIG. 14). Thus, the second support part 68 positioned on the plunger 16 side (the right side in FIG. 14) will constitute a stopper for inhibiting forward progress of the plunger 16, making forward progress of the plunger 16 impossible until the second support parts 68 are retracted from above the resting face 32, as will be described later.

Additionally, the peripheral walls 66, 70 formed on the first support parts 64 and the second support parts 68 will be positioned outwardly from the main body 26 of the intraocular lens 14. In the present embodiment in particular, the peripheral walls 66 that have been formed on the first support parts 64 will be positioned to either side of the intraocular lens 14 on a diagonal axis with respect to the axial direction of the tool body 12, while the peripheral walls 70 that have been formed on the second support parts 68 will be positioned to either side of the intraocular lens 14 in the axial direction of the tool body 12. The level of displacement of the intraocular lens 14 in the axial direction and axis-perpendicular direction relative to the tool body 12 will be restricted thereby, and the intraocular lens 14 will be held in stable fashion. Additionally, in a state of rest on the first and second support parts 64, 68, the main body 26 of the intraocular lens 14 will be positioned a prescribed distance away from the resting face 32, and supported in a noncontact state with respect to the resting face 32.

Then, intraocular lens 14 is set accommodated within the tool body 12 by bending the bending part 40 so that the opening 29 of the stage 24 is covered by the cover part 36. The cover part 36 will be maintained in the closed state through engagement of the catch piece 50 in the catch notch 54.

The intraocular lens 14 is accommodated in the insertion tool 10 is the above manner. The insertion tool 10 according to this embodiment, with the intraocular lens 14 accommodated therein, will then be subjected to a sterilization process etc., then packaged and shipped.

When the intraocular lens 14 is to be inserted into the eye using the insertion tool 10 according to the present embodiment, first, the support member 56 is pulled downward from the tool body 12 to detach it from the tool body 12. By so doing, the first and second support parts 64, 68 which were supporting the intraocular lens 14 will be withdrawn downwardly from the resting face 32 and retract below the resting face 32 so that the intraocular lens 14 now rests directly on the resting face 32. In the present embodiment, because the resting face 32 is a flat face, the intraocular lens 14 can be positioned resting stably thereon; and because the width dimension of the recessed slot 28 is slightly larger than the diameter dimension of the main body 26 of the intraocular lens 14, rotation of the intraocular lens 14 in the circumferential direction on the resting face 32 will be prevented as well.

Figure 15:
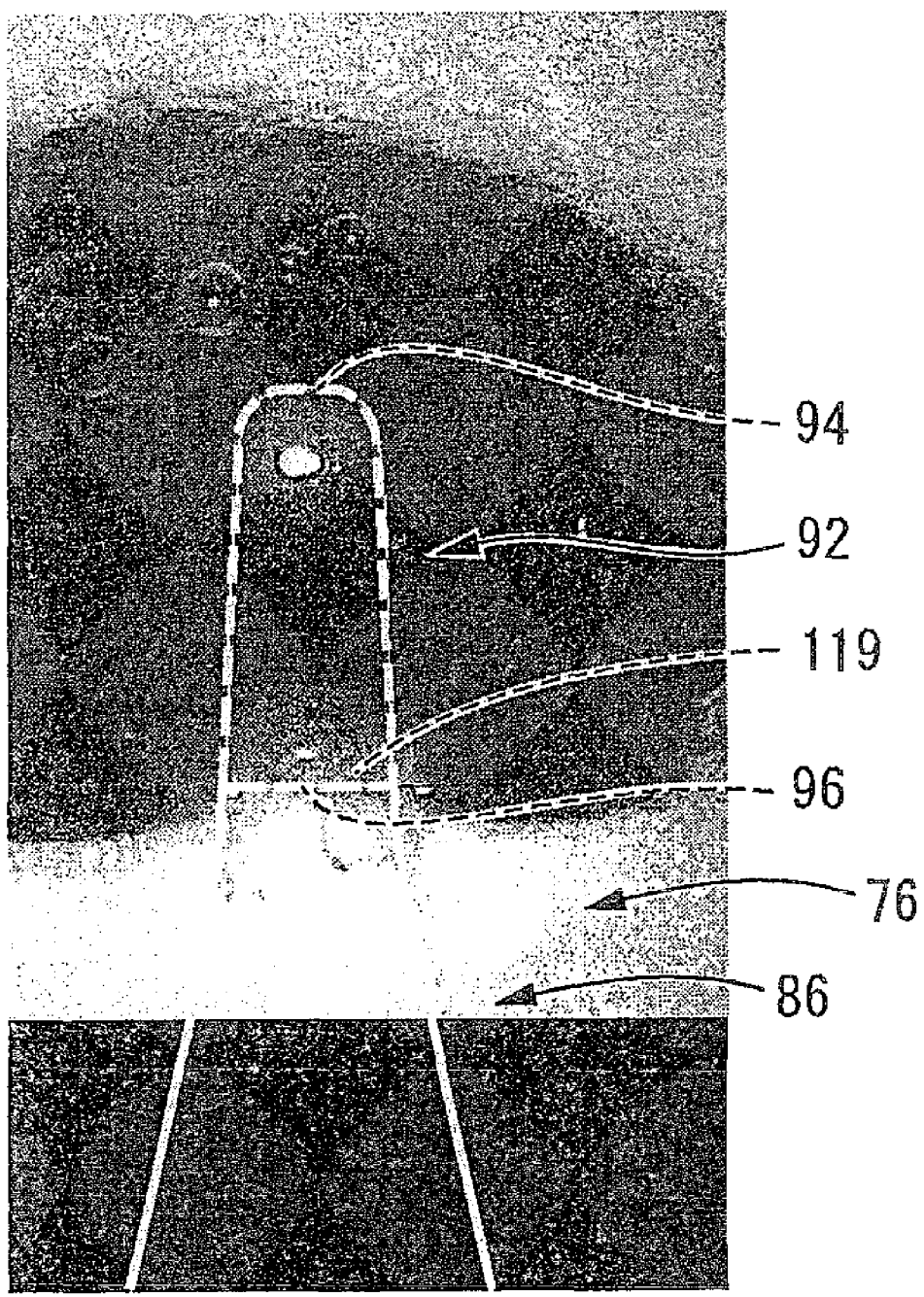
FIG. 15 is an view for explaining a way of operation of the intraocular lens insertion tool of FIG. 1.

Next, as depicted in FIG. 15, the inclined orifice 94 of the nozzle part 76 is inserted through a surgical incision 119 made in the ocular tissue. Here, because the recessed line 96 has been formed in the nozzle part 76, the recessed line 96 can be used as an indicator when ascertaining the insertion location, and the inclined orifice 94 can be positioned at an appropriate insertion location by inserting the inclined orifice 94 until the recessed line 96 lines up with the surgical incision 119.

Then, with the nozzle part 76 inserted through the surgical incision 119, the pusher plate 111 of the plunger 16 is pushed towards the tool body 12 side. By so doing, the tip of the plunger 16 will come into contact against the outside peripheral edge of the main body 26 of the intraocular lens 14 which is resting on the resting face 32, and the intraocular lens 14 will be guided towards the basal end orifice 80 by the plunger 16. At this point, the haptic 30 that is situated towards the plunger 16 side of the intraocular lens 14 will rest within the notch 105 of the plunger 16 so that the tip of the plunger 16 directly faces the outside peripheral face of the main body 26 of the intraocular lens 14 along an axis in the lens diametrical direction, thus avoiding entanglement of the haptic 30 when the main body 26 is contacted by the plunger 16.

Moreover, since the haptic 30 has been set within the notch 105 of the plunger 16, the mode of deformation of the haptic 30 will be limited to a certain extent in the course of the main body 26 of the intraocular lens 14 being pushed by the tip of the plunger 16. It will be possible thereby to prevent problems during pushing of the intraocular lens 14 with the plunger 16, such as unanticipated deformation of the haptic 30, adhesion of the haptic 30 to the main body 26, or catching of the haptic 30 inside the nozzle part 76, as well as deformation or rotation of the intraocular lens 14.

In the present embodiment in particular, the notch 105 takes the form of a single recessed slot extending in the generally axis-perpendicular direction on the upper face of the plunger 16; and the slot wall face lying towards the front side in the plunging direction of the plunger 16 is defined by an inclined face that flares out towards the orifice side of the recessed groove, whereby the haptic 30 of the intraocular lens 14 can be easily and reliably set within the recessed groove, i.e. the notch 105. Also, the slot wall face lying towards the back side in the plunging direction of the plunger 16 in the recessed groove, i.e. the notch 105, is defined by a vertical face that rises up approximately on the vertical towards the orifice of the slot from the slot base face; and during the plunging operation of the plunger 16, once the haptic 30 positioned within the notch 105 has been reliably guided into the notch 105 by the inclined face at the front side of the recessed groove (the notch 105), it will thereafter be effectively prevented from becoming dislodged from the recessed groove (the notch 105) so as to be stably held within recessed groove (the notch 105).

In preferred practice, prior to pushing the intraocular lens 14, an appropriate lubricant will be injected into the stage 24 or the nozzle part 76 if needed. In the present embodiment in particular, an injection hole 120 is formed passing through the cover part 36 in the thickness direction so that lubricant can be injected through the injection hole 120 with the cover part 36 closed. Alternatively, injection of lubricant could also be accomplished, for example, by injection through the inclined orifice 94 of the nozzle part 76; by opening the cover part 36 and injecting lubricant from the opening 29 of the stage 24; or by withdrawing the plunger 16 from the tool body 12 and injecting lubricant from the orifice at the back end of the through-bore 20.

During plunging of the plunger 16, the amount of displacement in the left-right direction by the rod-like part 100 of the plunger 16 will be limited by the guide projections 48, 48 formed on the cover part 36 and situated to either side. It will thus be possible for the plunger 16 to be plunged stably in the axial direction. Additionally, because the center guide plate part 46 and the left/right guide plate parts 44a, 44b project out towards the resting face 32, excessive upward displacement of the intraocular lens 14 will be limited, and it will be possible for the intraocular lens 14 to be guided smoothly inside the basal end orifice 80.

Figure 16:
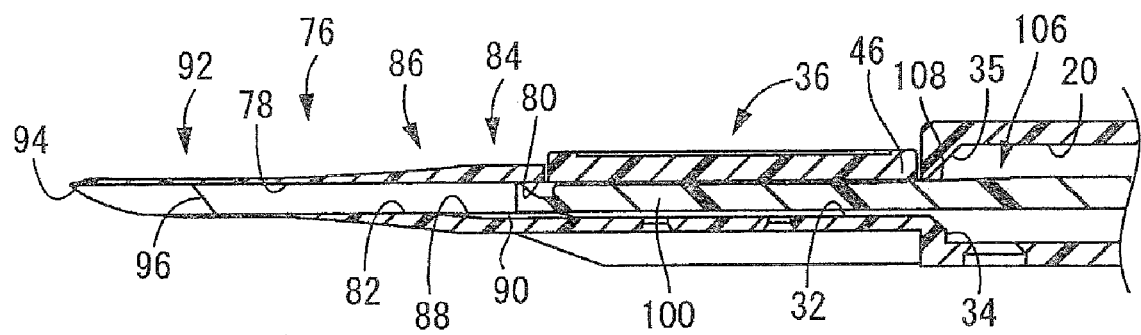
FIG. 16 is an axial cross sectional view of the intraocular lens insertion tool of FIG. 1.

In the present embodiment in particular, the upward projecting portion 106 is formed projecting up from the plunger 16, and the tapered face 108 is formed on the upper face of the upward projecting portion 106. As depicted in model form in FIG. 16, in the process of plunging the plunger 16, the upward projecting portion 106 will be disposed in sliding contact against the upper wall part 35 of the through-bore 20 via its tapered face 108. Since the tapered face 108 is defined as an inclined face that gradually juts upward to the rear in the axial direction of the rod-like part 100, as the plunger 16 is pushed ahead, the contact force with the upper wall part 35 exerted on the upward projecting portion 106 via its tapered face 108 will increase. Thus, the plunger 16 in the present embodiment will experience gradually higher operating resistance as it is pushed deeper into the tool body 12. In the present embodiment, the resistance graduating mechanism includes the upper wall part 35 of the tool body 12, and the tapered face 108 of the plunger 16 urged into contact with the upper wall part 35.

Also, the center guide plate part 46 that has been formed on the cover part 36 will come into contact with the upper face of the plunger 16. This acts to push the plunger 16 towards the resting face 32 so as to inhibit deformation and upward displacement of the plunger 16 so that it may be guided without appreciable separation from the resting face 32, making it possible for it to be pushed smoothly into the basal end orifice 80.

The intraocular lens 14 which has been guided into the guide part 84 from the basal end orifice 80 by the plunger 16 will then be pushed into the constricted-diameter part 86 as the center section of the main body 26 is induced to jut downward by the guide projecting parts 90, 90 that have been formed on the base face 82 of the guide part 84, thus bringing about initial deformation of the lens to a concave shape. Also, displacement and deformation of the rod-like part 100 of the plunger 16 in the axis-perpendicular direction will be limited by being held between the guide projecting parts 90, 90, making it possible for the plunger 16 to be pushed stably in the axial direction.

Furthermore, as the tip of the plunger 16 slips into the constricted-diameter part 86 it will come into contact with the inclined face 88 that has been formed at the axial back end part of the constricted-diameter part 86, thereby imparting a restraining sensation to the surgeon via the plunger 16. It will therefore be possible for the surgeon to discern that the tip of the plunger 16 has slipped into the constricted-diameter part 86, in other words, that the intraocular lens 14 has been pushed into the constricted-diameter part 86, and that the intraocular lens 14 has now begun to experience bowing deformation.

Next, as the plunger 16 is pushed along further, the intraocular lens 14 will be guided through the constricted-diameter part 86 towards the distal end and will experience bowing deformation to even smaller size, and will then be guided into the distal end part 92 of the nozzle part 76. In the present embodiment, because the recessed line 96 of slot form has been formed on the inside peripheral wall of the distal end part 92, the recessed line 96 will now act as an air bleed hole so that the intraocular lens 14 can be pushed more smoothly. That is, using the recessed line 96 as a marker, by plunging the plunger 16 to a location at which the front edge of the intraocular lens 14 reaches the recessed line 96 inside the nozzle part 76 it will be possible to rapidly expel any remaining air inside the nozzle part 76.

Then, by pushing the plunger 16 further, the intraocular lens 14 will be guided into the inclined orifice 94 of the nozzle part 76. In this regard, in the present embodiment in particular, since the inclined orifice 94 has a diagonal orifice shape it will be possible for the intraocular lens 14 to emerge to the outside of the insertion tool 10 in small increments with increasing plunging stroke of the plunger 16. By so doing, the recovery force produced by the inherent elasticity of the intraocular lens 14 will be manifested gradually, thus reducing the risk of a sudden release of recovery force which could cause the intraocular lens 14 to pop out. At the same time, this decreasing resistance of the intraocular lens 14 to the pushing force of the plunger 16 due to gradual emergence of the intraocular lens 14 to the outside while being guided into the inclined orifice 94 will be accompanied by increasing operating resistance of the plunger 16 due to gradual increasing contact force exerted on the upward projecting portion 106 by the plunger 16 as described above, thereby making it possible to provide the surgeon with a generally unchanging level of operating resistance. At a minimum, it will suffice for increasing operating resistance by the resistance graduating mechanism to be exhibited beginning at the point in time that the intraocular lens 14 starts to gradually emerge from the inclined orifice 94; for example, it would be acceptable for the operating resistance to begin to increase gradually immediately after initiation of the plunging operation of the plunger 16, as described in the present embodiment. The intraocular lens 14 will then be pushed out from the insertion tool 10 through the inclined orifice 94 and be inserted into the eye.

Figure 17:
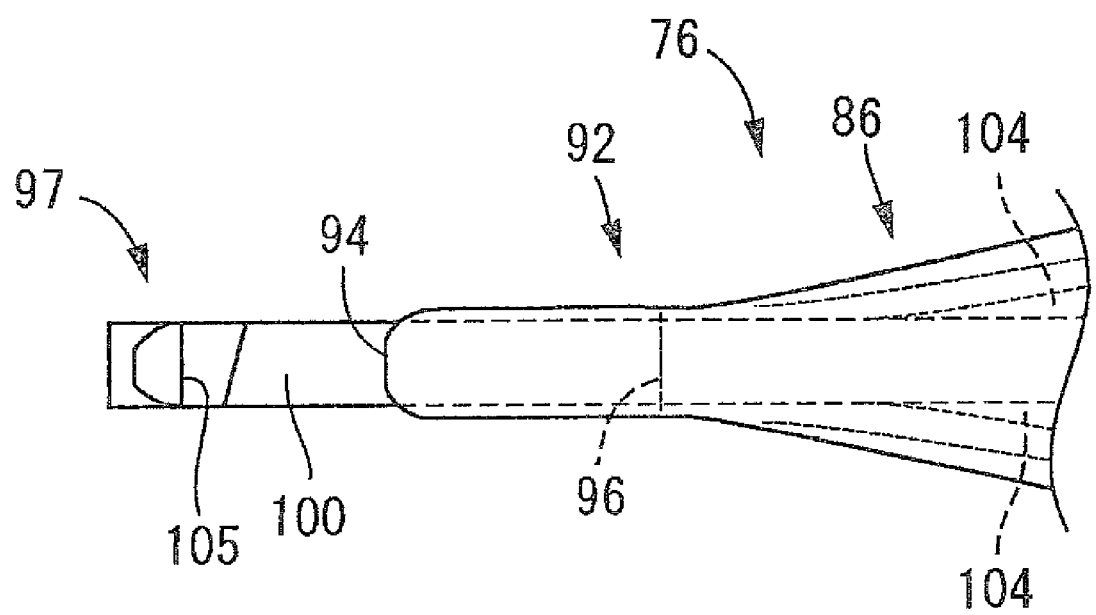
FIG. 17 is a fragmental top plane view of the intraocular lens insertion tool of FIG. 1 for showing projecting end position of the plunger.

In the present embodiment in particular, the plunging operation is carried out with the haptic 30 that is situated to the back side of the intraocular lens 14 in the plunging direction of the plunger 16 positioned inside the notch 105 that has been formed at the tip of the plunger 16. For this reason, the position at which the plunger 16 is situated with the notch 105 projecting out completely from the inclined orifice 94 as depicted in FIG. 17 in order that the haptic 30 that has been positioned inside the notch 105 may completely disengage is designated as the maximum plunging position. This maximum plunging position will be limited due to the distal end face of the pass-through part 98 of the plunger 16 engaging with the upper and lower wall parts 35, 34 of the tool body 12; in the present embodiment, the stopper mechanism for the plunger 16 includes these upper and lower wall parts 35, 34. This stopper mechanism will also prevent the plunger 16 from projecting out excessively from the inclined orifice 94, thus improving safety during the insertion operation. As will be appreciated from the above, in the present embodiment, the plunging zone of the plunger 16 has a range extending from the axial back edge of the resting face 32 to the inclined orifice 94.

In the insertion tool 10 having the above construction, the main body 26 of the intraocular lens 14 is supported at its outside peripheral section only by the first and second support parts 64, 68 so as to be supported in a state of noncontact above and away from the resting face 32, thus reducing the risk of damage to the center section of the main body 26. Displacement of the intraocular lens 14 will be limited by the peripheral walls 66, 70 provided on the first and second support parts 64, 68 so that the intraocular lens 14 can be stably supported and can rest above the resting face 32 with excellent precision of positioning.

Additionally, in the present embodiment, the catch hooks 72 that hold the support member 56 in a state of attachment to the tool body 12 and that hold the first and second support parts 64, 68 in a state of projection above the resting face 32 have been integrally formed with the second support parts 68. It will therefore be possible for the second support parts 68 to be disposed in direct engagement with the resting face 32 and for the first and second support parts 64, 68 to project precisely from prescribed locations on the resting face 32, and advantageously held in this projecting state. The locking mechanism for attaching the support member 56 to the tool body 12 can be produced with excellent space efficiency, and a restraining sensation can be imparted when the catch hooks 72 have been successfully projected up from the resting face 32, so that it can be ascertained that the support member 56 has been attached correctly.

When using the insertion tool 10 of the present embodiment, it is possible for the intraocular lens 14 to be rested on the resting face 32 by a very simple operation, namely, of detaching the support member 56 from the tool body 12. In the insertion tool 10 of the present embodiment, since consistent precision of positioning is afforded by the first and second support parts 64, 68 as mentioned previously, despite the simplicity of the operation it will be possible for the intraocular lens 14 to be rested on the resting face 32 with excellent positioning accuracy. Further, because the intraocular lens 14 is rested with the opening 29 of the stage 24 maintained covered by the cover part 36, the intraocular lens 14 can be prevented from falling out from the insertion tool 10. A hygienic advantage is provided as well, due to reduced likelihood of contact of the intraocular lens 14 with the outside environment.

Additionally, in the insertion tool 10 of the present embodiment, the inclined orifice 94 is defined as an inclined orifice that opens on the diagonal with respect to the center axis of the nozzle part 76. Thus, the ejecting action produced by the elasticity of the intraocular lens 14 will be manifested in gradual increments, thus reducing the risk of that the intraocular lens 14 will suddenly pop out from the inclined orifice 94.

Also, in the present embodiment, the resistance graduating mechanism for gradually increasing the contact force of the plunger 16 exerted on the upward projecting portion 106 includes the upper wall part 35 of the tool body 12, and the tapered face 108 of the plunger 16 that is disposed in contact against the upper wall part 35; and is designed so that operating resistance of the plunger 16 will increase as the plunger 16 is plunged forward. It will be possible thereby to avoid a situation in which accelerating ejection action is exerted on the intraocular lens 14 before the surgeon realizes it; and to push the intraocular lens 14 along at generally constant speed through the entire plunging process.

Specifically, due to the diagonal shape of the inclined orifice 94, the intraocular lens 14 that has been guided into the inclined orifice 94 will emerge to the outside gradually, and the ejecting action produced by the elasticity of the lens per se will increase gradually. In other words, the resistance of intraocular lens 14 to the pushing force of the plunger 16 will gradually decrease when the intraocular lens 14 is guided into the inclined orifice 94. Notwithstanding, if the surgeon operates the plunger 16 at a constant level of force, there is a risk that accelerating ejection action will be exerted on the intraocular lens 14, causing the intraocular lens 14 to pop out. Accordingly, in the present embodiment, due to the resistance graduating mechanism, it will be possible for the operating resistance of the plunger 16 to increase gradually as the intraocular lens 14 gradually emerges from the inclined orifice 94. Thus, through a combination of gradually decreasing resistance to the pushing force of the plunger 16 due to the inclined orifice 94, and gradually increasing operating resistance of the plunger 16 due to the resistance graduating mechanism, it will be possible for the first time to impart generally constant operating resistance to the plunger 16, making it possible for the surgeon to carry out the lens ocular insertion procedure in the intended fashion at generally unchanging speed.

Additionally, in the insertion tool 10 constructed in accordance with the present embodiment, the resistance graduating mechanism has a simple construction composed of the upper wall part 35 of the tool body 12 and the tapered face 108 of the plunger 16, whereby the weight of the insertion tool 10 can be reduced, and the ease of handling and control of the insertion tool 10 can be improved.

While the invention has been described detail herein in terms of a single preferred embodiment, this embodiment is merely exemplary, and the specific disclosure herein should not be construed as limiting in any way.

Figure 18:
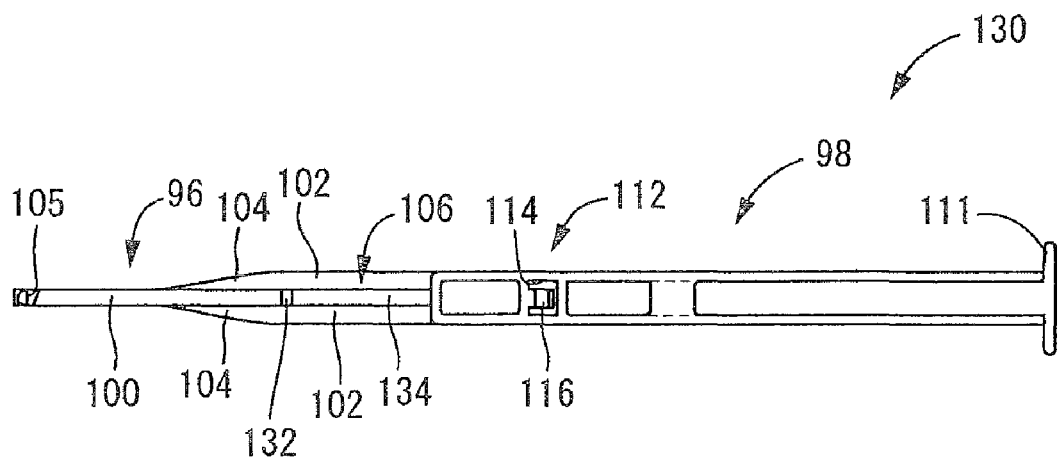
FIG. 18 is a top plane view of a plunger of the intraocular lens insertion tool according to a second embodiment of the present invention.
Figure 19:
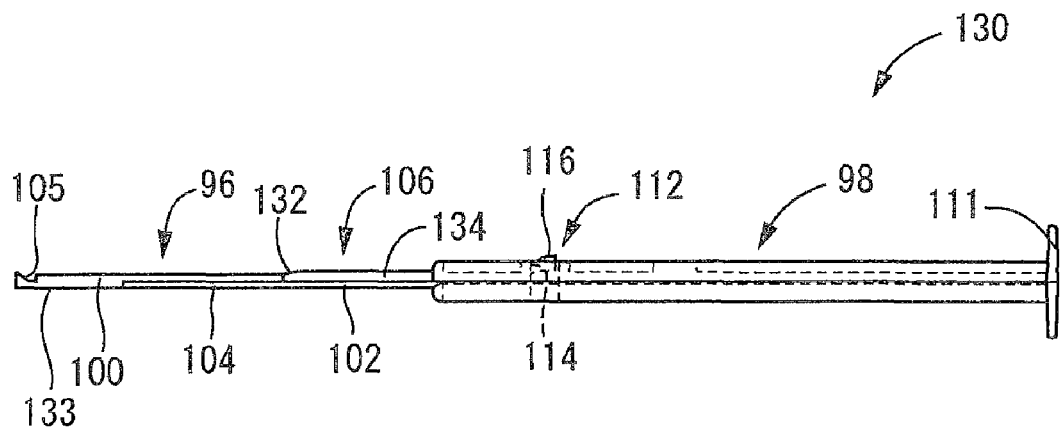
FIG. 19 is a side elevational view of the plunger of the intraocular lens insertion tool of FIG. 18.

For example, the specific structure of the resistance graduating mechanism for gradually increasing the operating resistance of the plunger member is not limited to the one described in the preceding first embodiment. FIGS. 18 and 19 depict a plunger 130 provided as the plunger member in a second embodiment of the present invention. In the present embodiment, only the shape of the plunger member differs from that in the first embodiment, and accordingly only the plunger 130 is shown. In the following description, elements that are substantially identical to those in the preceding first embodiment are assigned like symbols in the drawings, with no description provided.

The plunger 130 has a tapered face of different length dimension in the axial direction than the tapered face 108 of the plunger 16 of the preceding first embodiment. Specifically, the tapered face 132 that is formed projecting from the upper face of the rod-like part 100 of the plunger 130 is defined with its axial front edge part situated slightly rearward from the rear edge part of the pointed parts 104 of the flattened parts 102, and its axial rear edge part situated slightly rearward from its axial front edge part. By so doing, the tapered face 132 of the plunger 130 will have axial length dimension that is sufficiently smaller in comparison with the tapered face 108 of the plunger 16 of the first embodiment, and will be imparted with a steeper angle of incline. A flat part 134 that extends in the axial direction with unchanging height dimension is formed at the rear edge part of the working part 97 from the rear edge part of the tapered face 132. By so doing, the plunger 130 in the present embodiment will have gradually increasing cross section towards the rear in the axial direction from the axial front edge part to the axial rear edge part of the pointed parts 104 in the flattened parts 102, and from the axial front edge part to the axial rear edge part of the tapered face 132.

Figure 20:
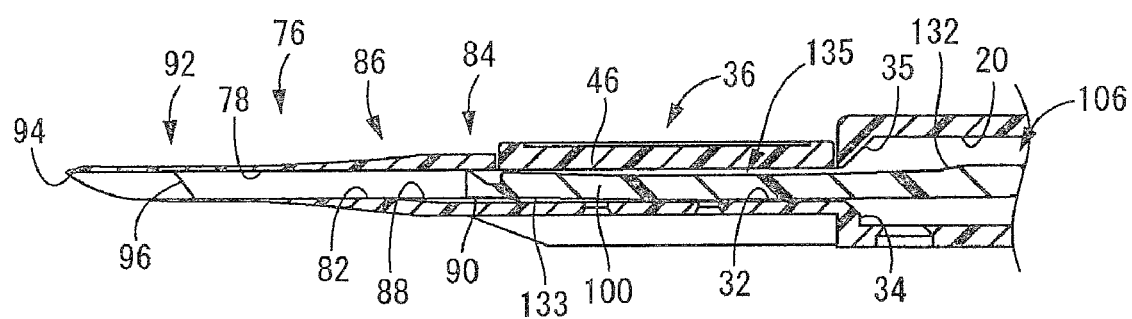
FIG. 20 is a cross sectional view of the intraocular lens insertion tool according to the second embodiment.

The plunger 130 of this structure will be inserted into a tool body 12 of a structure similar to that of the first embodiment described previously. As depicted in model form in FIG. 20, when the plunger 130 of the present embodiment is pushed in, the distal end part of the base face 133 of the rod-like part 100 will first undergo upward displacement in sliding contact against the guide projecting parts 90. As the plunger 130 is pushed in further, the upward projecting portion 106 of the plunger 130, via its tapered face 132, will become positioned in sliding contact against the upper wall part 35 that has been formed on the front end face of the through-bore 20 of the tool body 12 and the plunger 130 will be displaced downwardly by the upper wall part 35. The base face 133 and the upward projecting portion 106 will thereby be restrained by the guide projecting parts 90 and the upper wall part 35, and between the guide projecting parts 90 and the upper wall part 35, the plunger 130 as a whole will experience elastic deformation in an upwardly concave deflected condition. In the present embodiment, the upward projecting portion 106 and the base face 133 of the rod-like part 100 of the plunger 130 constitute the sliding parts, and the guide projecting parts 90 and the upper wall part 35 that are disposed in contact with them constitute the contact parts. A deflection zone 135 forms between the guide projecting parts 90 and the upper wall part 35.

Here, the pointed parts 104 give the plunger 130 increasing width dimension moving towards the back, while the tapered face 132 gives it increasing height dimension moving towards the back. A cross section variation portion that includes the pointed parts 104 and the tapered face 132 is thereby formed in the medial section in the axial direction of the plunger 130; as the plunger 130 is pushed in, the large-cross sectional area section of the plunger 130 which is positioned within the deflection zone 135 will become longer. As a result, deflection reaction force will increase, the level of vertical reaction force acting as deflection reaction force on the guide projecting parts 90 and the upper wall part 35 will gradually vary, and hence frictional resistance of the base face 133 and the upward projecting portion 106 with respect to the guide projecting parts 90 and the upper wall part 35 will increase gradually in association therewith. Thus, the operating resistance of the plunger 130 will increase gradually. Thus, in the present embodiment, the resistance graduating mechanism includes the guide projecting parts 90 and the upper wall part 35 as the contact parts; the deflection zone 135; and the pointed parts 104 and tapered face 132 that constitute the cross section variation portion of the plunger 130.

While the tapered faces 108, 130 formed on the plungers 16, 130 in the preceding first and second embodiments each have constant slope angle, it would be acceptable for example for the slope angles of these tapered faces 108, 130 to vary in the axial direction of the plungers 16, 130. By so doing, the contact force exerted onto the upward projecting portion 106 via the tapered face 108, 130 can be adjusted to a higher degree, and the operating resistance of the plunger 16, 130 can be adjusted to a higher degree.

Further, it would also be possible to provide the tool body 12 with an inclined face adapted for sliding contact against the sliding part of the plunger member. For example, rather than the tapered face 108, a vertical face could be formed on the axial front end face of the upward projecting portion 106 as the sliding part of the plunger 16 as in the preceding first embodiment; and an inclined face that gradually approaches the upward projecting portion 106 towards the front in the axial direction could be formed on the lower end face of the upper wall part 35 by way of the sliding part formed on the tool body 12, in order to constitute the resistance graduating mechanism.

It is not essential for the locking mechanism that fastens the support member 56 to the tool body 12 to be formed on the second support parts 68, as were the catch hooks 72 formed on the second support parts 68 described earlier. In place of the catch hooks 72, it would be possible for example to give the first support parts 64 and the second support parts 68 contours with gradually increasing dimension in top view towards the leg plate part 62 side, and by forcing these first support parts 64 and the second support parts 68 into the through-holes 74 formed the resting face 32, to fasten the support member 56 to the back side of the resting face 32 through the recovery force of the through-holes 74 and frictional force between the members; or to fasten the side wall parts 58 of the support member 56 by clasping them between the downward projecting walls 37 (see FIG. 5) that project downward from the widthwise edges of the resting face 32.

The intraocular lens insertion tool of the present invention is not limited to being provided with the intraocular lens housed therein beforehand as described in the preceding embodiments, and may be provided separately from the intraocular lens, with the intraocular lens be set in the tool at the time of surgery.

Furthermore, while the intraocular lens 14 accommodated in the insertion tool 10 has a main body 26 and haptics 30 that are formed as separate elements, it would of course be possible for the main body 26 and the haptics 30 to be integrally formed by the same component.

What is claimed is:

1. An intraocular lens insertion tool for accommodating an intraocular lens, comprising:
    a tool body having generally tubular shape for accommodating the intraocular lens, and including an insertion tube section disposed at a distal end section of the tool body in an axial direction; and
    a plunger member adapted to be inserted into the tool body from a rear in the axial direction and adapted to be moved forward to insert into an eye the intraocular lens such that the intraocular lens undergoes compact deformation in association with forward displacement in the axial direction by the plunger member and is adapted to be pushed out through the insertion tube section,
    wherein the insertion tube section has at a distal end thereof an inclined orifice that opens diagonally with respect to a center axis of the insertion tube section,
    the plunger member is furnished with a sliding part that is remote from a distal end portion thereof and slides against the tool body during displacement thereof in a direction of plunging into the tool body,
    a resistance graduating mechanism is provided to gradually increase operation resistance of the plunger member by gradually increasing contact force exerted on the sliding part as the intraocular lens gradually emerges from the inclined orifice through plunging of the plunger member into the tool body, and
    the resistance graduating mechanism is constituted by providing an inclined face inclined with respect to a plunging direction of the plunger member, to at least one of the sliding part of the plunger member, and a contact portion provided on the tool body and adapted to slide against the sliding part during plunging of the plunger member.

2. The intraocular lens insertion tool according to claim 1, wherein the resistance graduating mechanism is constituted by providing a deflection zone adapted to produce elastic deformation of the plunger member in a prescribed lengthwise section of the axial direction through pressing of the contact portion against the sliding part; and providing in the deflection zone a cross section variation portion of gradually increasing cross sectional area of the plunger member in a plunging direction of the plunger member.

3. The intraocular lens insertion tool according to claim 1, wherein the insertion tube section is formed by a light-transmissive component; and a visible marker line extending in a circumferential direction of the insertion tube section is formed at a prescribed location axially to a rear of the inclined orifice in the insertion tube section.

4. The intraocular lens insertion tool according to claim 1, wherein the plunger member has a notch that is disposed at a distal end section thereof, and that is adapted to hold a rear one of a pair of haptics of the intraocular lens extending to either side, which are adapted to be set facing in the axial direction of the tool body.

5. The intraocular lens insertion tool according to claim 1, wherein the tool body has a resting portion disposed in communication with a basal end of the insertion tube section, the resting portion is provided with a resting face on which the intraocular lens is adapted to rest and an opening that opens to an outside of the tool body; and the tool body is furnished with a cover body disposed covering the opening, with the plunger member adapted to be pushed towards the resting face by the cover body.

6. The intraocular lens insertion tool according to claim 5, wherein a pair of guide projecting parts extending in the axial direction are formed on a bottom face at an axial front of the resting face in the tool body, and the plunger member is adapted to be guided between the guide projecting parts.

7. The intraocular lens insertion tool according to claim 1, wherein a step adapted to contact the plunger member inside a plunging zone of the plunger member is provided in the tool body.

8. The intraocular lens insertion tool according to claim 1, wherein through-holes are formed in a resting face on which the intraocular lens is adapted to rest, a support member defined as a separate part from the tool body is attached to the resting face from an outside, and an outside peripheral support portion to support an outside peripheral portion of the intraocular lens is constituted by passing support portions formed on the support member through the through-holes so as to project out above the resting face; and catch hooks adapted to catch on the resting face and prevent the support portions from dislodging from the resting face and to maintain the support portions in a state projecting out from the resting face are formed on the support portions.

* * * * *

UNITED STATES PATENT AND TRADEMARK OFFICE
CERTIFICATE OF CORRECTION

| | | |
|---|---|---|
| PATENT NO. | : 8,080,017 B2 | |
| APPLICATION NO. | : 12/318227 | |
| DATED | : December 20, 2011 | |
| INVENTOR(S) | : Masayoshi Tanaka | |

It is certified that error appears in the above-identified patent and that said Letters Patent is hereby corrected as shown below:

Title Page

Please correct the name of the Assignee as follows:

(73)   Assignee:   Kowa Company, Ltd.

Signed and Sealed this
Twentieth Day of March, 2012

David J. Kappos
*Director of the United States Patent and Trademark Office*